(12) United States Patent
Guerrero et al.

(10) Patent No.: US 8,753,680 B2
(45) Date of Patent: Jun. 17, 2014

(54) CAPSULE FOR THE PREVENTION OF CARDIOVASCULAR DISEASES

(75) Inventors: Marta Guerrero, Barcelona (ES); Anna Orriols, Manresa (ES); Pablo Martin, Barcelona (ES); Manel Raga, Barcelona (ES)

(73) Assignees: Ferrer Internacional S.A., Barcelona (ES); Fundacion Central Nacional de Investigaciones Cardiovasculares Carlos III, Madrid (ES)

( * ) Notice: Subject to any disclaimer, the term of this patent is extended or adjusted under 35 U.S.C. 154(b) by 249 days.

(21) Appl. No.: 12/934,942

(22) PCT Filed: Mar. 25, 2009

(86) PCT No.: PCT/EP2009/053545
§ 371 (c)(1),
(2), (4) Date: Dec. 27, 2010

(87) PCT Pub. No.: WO2009/118359
PCT Pub. Date: Oct. 1, 2009

(65) Prior Publication Data
US 2011/0086094 A1    Apr. 14, 2011

(30) Foreign Application Priority Data
Mar. 28, 2008  (EP) .................................. 08153615

(51) Int. Cl.
*A61K 9/58* (2006.01)
(52) U.S. Cl.
USPC ......................................................... 424/462

(58) Field of Classification Search
None
See application file for complete search history.

(56) References Cited

U.S. PATENT DOCUMENTS

| | | | |
|---|---|---|---|
| 2003/0068366 A1* | 4/2003 | Chungi et al. | 424/452 |
| 2007/0009591 A1 | 1/2007 | Trivedi et al. | |
| 2007/0116756 A1* | 5/2007 | Komireddi et al. | 424/451 |
| 2007/0166375 A1 | 7/2007 | Patel et al. | |
| 2008/0014271 A1* | 1/2008 | Goffin et al. | 424/476 |

FOREIGN PATENT DOCUMENTS

| | | | | |
|---|---|---|---|---|
| EP | 1 657 265 A1 | | 5/2006 | |
| WO | WO 01/58429 | * | 8/2001 | ............... A61K 9/20 |
| WO | WO 01/58429 A1 | | 8/2001 | |
| WO | WO 03/020243 A1 | | 3/2003 | |
| WO | WO 2004/080488 A2 | | 9/2004 | |
| WO | WO 2005/011586 A2 | | 2/2005 | |
| WO | WO 2009/022821 A2 | | 2/2009 | |

OTHER PUBLICATIONS

International Preliminary Report on Patentability dated Jul. 23, 2010, issued in PCT/EP2009/053545.
International Search Report dated Mar. 3, 2010, issued in PCT/EP2009/053545.

\* cited by examiner

*Primary Examiner* — Brian Gulledge
(74) *Attorney, Agent, or Firm* — Birch, Stewart, Kolasch & Birch, LLP (57) ABSTRACT

The invention relates to a capsule for the prevention of cardiovascular diseases which comprises coated tablets of acetylsalicylic acid, coated tablets of simvastatin or pravastatin, and coated tablets of lisinopril, ramiphl or perindopril. The capsules are used for the prevention of cardiovascular diseases in high-risk populations.

12 Claims, 1 Drawing Sheet

CAPSULE FOR THE PREVENTION OF CARDIOVASCULAR DISEASES

FIELD OF THE ART

The invention relates to pharmaceutical compositions for the prevention of cardiovascular diseases in high-risk patients. More specifically, the invention relates to a capsule comprising a combination of acetylsalicylic acid, an inhibitor of 3-hydroxy-3-methylglutaryl-coenzyme A (HMG-CoA) reductase chosen from a simvastatin compound and a pravastatin compound, and an inhibitor of the angiotensin converting enzyme (ACE) chosen from a lisinopril compound, a ramipril compound and a perindopril compound.

STATE OF THE ART

Cardiovascular disease is the main cause of mortality and morbidity in the developed world and it is becoming the main cause of mortality and morbidity worldwide. Although cardiovascular risk factors are well known, control thereof is below optimal, even in the most developed countries. Changes in eating habits and lifestyle undoubtedly reduce cardiovascular risk. Nevertheless, not enough work has been carried out to identify the most efficient and cost-effective way of implementing these changes in lifestyle. On the other hand, the treatment and prevention of cardiovascular disease is expensive and its cost is increasing.

The low compliance with prescribed and self-administered treatments is well known to be a great problem in treating chronic diseases, such as in the case of cardiovascular disease. Compliance with chronic treatments is estimated at 50% in developed countries. The implications of poor compliance with treatments are important both for the individual and for society. For the patient, treatment benefits are reduced, producing infra-treatment and making it more difficult for the clinician to evaluate its effectiveness and to determine the best dosage for such treatments. For society, poor compliance leads to generating chemical waste, an increase in health costs and self-medication.

Dosage complexity and adverse effects are the factors related to the drug that most affect prescription compliance. Both dosage complexity and adverse effects rapidly increase with the use of multiple therapies for the disease to be treated or with the treatment of more than one disease in the same patient, giving rise to less compliance with the medication.

In this context, Wald and Law (Br. Med. J. 326, No. 7404, 1419-23, 2003) defined the term "polypill", referring to the combination of drugs such as statins, anti-hypertensive agents, aspirin and vitamins, such as folic acid, for use in a single daily intake. The term statins includes 3-hydroxy-3-methylglutaryl-coenzyme A (HMG-CoA) reductase-inhibiting compounds. And aspirin has the chemical name acetylsalicylic acid. These authors recommend the use of the polypill as the way to achieve an important effect in the prevention of cardiovascular disease with minimal adverse effects based on a meta-analysis carried out with random short-term clinical studies. The strategy of the polypill containing several effective components for decreasing cardiovascular risk factors would thus prevent a high incidence of heart attacks and strokes. They concluded that the polypill strategy would be safe and that its generalized use would have a greater impact in cardiovascular disease prevention in occidental countries than any other intervention and they estimated that the polypill could reduce the incidence of coronary disease and ictus in up to 88 and 80%, respectively.

The authors analysed the most suitable patients for polypill intake. The candidates would be patients who had suffered an acute coronary syndrome or a brain ischaemic attack, patients with stable chronic angina, transitory ischaemic episodes and diabetics. Among the population without prior disease, the most determining factor is age such that 96% of deaths by acute coronary syndrome or ictus occur in people over 55 years of age, and preventive treatment for people over 55 years of age would prevent almost all of these deaths. That is, the best strategy would be to treat all patients with ischaemic disease and all people over 55 years of age.

Several patents have thus been published regarding polypills for cardiovascular use.

Patent application US2004219208 deals with sustained release medicinal products comprising an angiotensin II antagonist combined with one or more drugs chosen from compounds used in hypertension, hypoglycaemic drugs, lipid-lowering agents, antithrombotics, products for menopause and cytostatic drugs.

U.S. Pat. No. 6,576,256 deals with the combination of a hypocholesterolaemic drug such as an HMG-CoA reductase inhibitor, a renin-angiotensin system inhibitor, such as an ACE inhibitor, aspirin and at least one vitamin chosen from Vitamin B6, Vitamin B12 and folic acid.

Patent application WO03/020243 deals with the combination of a lipid-lowering agent, a renin-angiotensin system inhibitor and aspirin, and optionally at least one vitamin chosen from Vitamin B6, Vitamin B12 and folic acid.

Patent application WO2004/080488 deals with combinations of acetylsalicylic acid, HMG-CoA reductase inhibitors and anti-hypertensive substances chosen from calcium antagonists, ACE inhibitors, angiotensin II antagonists and diuretics.

Patent application WO2005/011586 deals with the combination of a β-adrenergic receptor antagonist or a diuretic, or both, a hypocholesterolaemic drug such as an HMG-CoA reductase inhibitor, a renin-angiotensin system inhibitor such as an ACE inhibitor, and aspirin.

Patent application WO2005/025673 deals with the combination of a hypoglycaemic agent of the biguanid family such as metformin, a lipid-lowering agent chosen from HMG-CoA reductase inhibitors, bile acid sequestrants, probucol and fibric acid compounds, and an antihypertensive chosen from renin-angiotensin system inhibitors, which may in turn be chosen from ACE inhibitors, angiotensin II antagonists and renin inhibitors, β-blockers, diuretics and calcium channel antagonists. The invention also relates to the presence of other optional components such as platelet anti-aggregating agents of the salicylate family, such as acetylsalicylic acid amongst others, and of various vitamin derivatives.

Patent application WO2006/020522 deals with various combinations to be administered at the start of several emergency symptoms, with cardiovascular symptoms amongst these. Amongst these combinations are combinations of aspirin and a statin that further comprise, amongst other chosen compounds, an ACE inhibitor.

Patent application WO2006/135415 covers nanoparticles in microemulsions, wherein the drugs to be combined may be aspirin, policosanol, atenolol, metaprolol, nadolol, propranolol, diltiazem, nifedipine, verapamil, captopril, enalapril, lisinopril, losartan, losartan in combination with hydrochlorothiazide, olmesartan, lovastatin, pravastatin, simvastatin, atorvastatin, bile acid sequestrants, cholestiramine, colestipol, gemfibrozil, clofibrate, probucol, anti-inflammatory drugs and antibiotics in general. The compositions may also include a nutritional supplement chosen from choline, folic acid, vitamin B6, vitamin B12, niacin, niacin combined chromium, vitamin C, vitamin E, coenzyme Q10 and ω-3 oils or combinations thereof.

Patent CN1785196 deals with a combination of aspirin, folic acid, simvastatin and ramipril.

Patent application US2006177504 deals with combinations of one or more anti-inflammatory agents and one or more medicinal products for the prophylaxis of ictus and cardiovascular disorders, such as aspirin, clopidogrel, ticlopidine, combinations of dipyridamole with aspirin, dipyridamole, cilostazol, pentoxyphylline, HMG-CoA reductase inhibitors, ACE inhibitors, angiotensin receptor blockers, calcium channel blockers, as well as vasodilating, antihypertensive, platelet anti-aggregating agents and oral anticoagulants in general.

Patent application WO2006/105806 deals with compositions comprising a statin, a compound that suppresses the production or activity of angiotensin, an anti-inflammatory drug and at least one antioxidant. The statin can be chosen from lovastatin, simvastatin, pravastatin and fluvastatin, the compound that suppresses the production or activity of angiotensin can be chosen from angiotensin II antagonists and ACE inhibitors, such as valsartan, losartan, irbesartan, trandolapril, perindopril or ramipril, the anti-inflammatory drug is preferably acetylsalicylic acid and the antioxidant is a vitamin chosen from vitamin A, vitamin C and vitamin E.

Patent application WO2007/011524 deals with presentations for the daily intake of medicinal products comprising a hypoglycaemic agent that is a biguanid derivative, preferably metformin, a lipid-lowering agent, preferably simvastatin, an antihypertensive, preferably lisinopril, and aspirin, such that the active ingredients are presented separately in a same blister.

Patent application WO2007/027454, in connection with new dihydropyrimidines, deals with their combinations with antiplatelet agents, ACE inhibitors and lipid-lowering agents, amongst other families of pharmaceutical substances. Aspirin is cited amongst the antiplatelet agents, ramipril and lisinopril amongst the ACE inhibitors, and simvastatin and pravastatin amongst the lipid-lowering agents.

Patent application US2007116756 deals with compositions comprising therapeutic amounts of a hypocholesterolaemic agent, a renin-angiotensin system inhibitor, a diuretic, aspirin and optionally at least one β-adrenergic receptor blocker in a single-dose presentation, as well as procedures for their preparation, use and the treatment of patients with cardiovascular diseases.

Patent application WO2007/092270 deals with combinations or the combined therapy of an antiplatelet agent, a β-adrenergic receptor blocker, a RAAS (renin-angiotensin-aldosterone system) inhibitor and/or a cholesterol modifying agent, so that aspirin is amongst the possible antiplatelet agents and statins are amongst the cholesterol modifying agents. The RAAS inhibitor is a compound to be chosen from ACE inhibitors, angiotensin II antagonists and/or aldosterone blockers (spironolactone, eplerenone or derivatives thereof). Such combinations or combined therapies are claimed to reduce the mortality or morbidity caused by coronary artery diseases.

Patent CN101024082 relates to various formulations, comprised of sex hormones, lipid-lowering agents, anti-hypertensive agents, hypoglycaemic agents and anticoagulants, to be used in the prevention and treatment of cardiocerebral diseases. Statins can be found amongst the lipid-lowering agents, ACE inhibitors amongst the antihypertensives and aspirin amongst the anticoagulants.

US 2003/0049314 relates to an oral dosage form containing a combination of a therapeutically effective unit dosage of a cholesterol-lowering agent, a therapeutically effective unit dosage of an inhibitor of the rennin-angiotensin system, a therapeutically effective unit dosage of aspirin and a pharmaceutically acceptable carrier.

In India, Torrent Pharma has commercialised CVpill, the first cardiovascular polypill. CVpill is presented in a single kit containing a capsule and a tablet. The capsule contains 10 mg of atorvastatin in powder, 5 mg of ramipril in powder and a 75 mg tablet of aspirin formulated with an enteric coating. The tablet contains metoprolol succinate 50 mg formulated for delayed release. The capsule and the tablet are to be taken simultaneously once a day.

Patent IN2003MU00153 relates to a combipack that may comprise: a) a statin and aspirin, b) a statin, aspirin and a β-blocker, c) a statin, aspirin, a β-blocker and an ACE inhibitor, and d) a statin, aspirin, a β-blocker and an angiotensin II antagonist. In all cases each one of the components is packed individually in the corresponding blister.

Currently the medical community indicates the need for having combinations of acetylsalicylic acid, hypocholesterolaemic agents, preferably HMG-CoA reductase inhibitors, and antihypertensives, preferably ACE inhibitors, comprising optimal doses of the three active ingredients in a single dosage form for the prevention of cardiovascular events in high risk populations (Schieffer B et al., Role of 3-hydroxy-3-methylglutaryl Coenzyme A reductase inhibitors, angiotensin-converting enzyme inhibitors, cyclooxygenase-2 inhibitors, and aspirin in anti-inflammatory and immunomodulatory treatment of cardiovascular diseases. *Am J. Cardiol.* 2003 Jun. 19; 91(12A):12H-18H. Review; Takeda T et al., Relationship between effects of statins, aspirin and angiotensin II modulators on high-sensitive C-reactive protein levels. *Atherosclerosis.* 2003 July; 169(1):155-8; Hippisley-Cox J et al., Effect of combinations of drugs on all cause mortality in patients with ischaemic heart disease: nested case-control analysis. *BMJ.* 2005 May 7; 330(7499): 1059-63; Kulkarni S P et al., Long-term adherence with cardiovascular drug regimens. *Am Heart J.* 2006 January; 151(1): 185-91; Gaziano T A et al., Cardiovascular disease prevention with a multidrug regimen in the developing world: a cost-effectiveness analysis. *Lancet.* 2006 Aug. 19; 368(9536):679-86. Review; and Choudhry N K et al., Should patients receive secondary prevention medications for free after a myocardial infarction? An economic analysis. *Health Aff (Millwood).* 2007 January-February; 26(1): 186-94). In particular, high-risk populations are understood as people of more than 55 years of age, patients with a background of angor pectoris, ictus, arteriosclerosis, intermittent claudication, diabetes, coronary disease, peripheral vascular disease, altered platelet function, haemodialysis, hypercholesterolaemia, hypertension, myocardial infarction, congestive heart failure, ischaemia, nephropathy, cardiac arrest or restenosis, smokers, obese people and sedentary people.

Despite the fact that all state of the art inventions somehow claim combinations of acetylsalicylic acid, HMG-CoA reductase inhibitors and ACE inhibitors, only patent application WO2004/080488 describes a specific example of a combination of the three active ingredients without further components. Thus, example 18 describes a combination in the form of tablets containing 100 mg of aspirin, 10 mg of simvastatin and 20 mg of lisinopril, and similarly, example 19 describes another composition also in the form of tablets containing 100 mg of aspirin, 40 mg of simvastatin and 8 mg of perindopril. However, the examples are very briefly described and they lack sufficient description in order to be carried out in practice.

On the other hand, depending on each patient's background it may be necessary for the medical community to have the availability of a wide range of possible polypills from which to choose according to each patient. This is one of the main obstacles that slows down the implementation of these therapies since it is frequently difficult to find a combination that adapts in its quantitative composition to the requirements of an individual patient. This situation becomes more urgent every day, given the sensitivity of society in general, which demands increasingly more personalised therapies every day.

However, any current pharmaceutical technology that tries to put the aforementioned inventions into practice finds the obstacle that changes in the dosage of the components is not easily performed, which produces extra costs and delays when introducing quantitative changes in the formulas during the manufacturing procedures.

Therefore, on the one hand it is necessary to provide society and the medical community with combinations of acetylsalicylic acid, HMG-CoA reductase inhibitors and ACE inhibitors at fixed doses, all in a same dosage form, but such that the fixed doses may in turn be easily customized to the individual characteristics of each patient or subgroup of the population. All this presents problems in the size of the dosage form and the compatibility between the different components that must be solved.

SUMMARY OF THE INVENTION

In this sense the present invention offers new compositions in the form of capsules comprising a variable number of acetylsalicylic acid tablets, a variable number of tablets of an HMG-CoA reductase inhibitor and a variable number of tablets of an ACE inhibitor, such that the number of tablets of each active ingredient can be customized to the characteristics of the individual patients or subgroups of the population they are intended for.

For the present invention simvastatin and pravastatin have been chosen from the HMG-CoA reductase inhibitors since they figure amongst those most widely prescribed in therapy for hypercholesterolaemia. For its part, pravastatin used as a sodium salt is extremely advantageous at the formulation level given its solubility in water. Similarly, lisinopril, ramipril and perindopril figure amongst the most widely prescribed ACE inhibitors in hypertension therapy. From the pharmacotechnical point of view lisinopril has the advantage over other compounds of the same family that it is obtained with less impurities and that used as a dihydrate it turns out to be one of the most soluble in water. Similarly, perindopril used as an erbumine salt is also freely soluble in water, which results in greater ease of absorption.

DETAILED DESCRIPTION OF THE INVENTION

Figure 1:
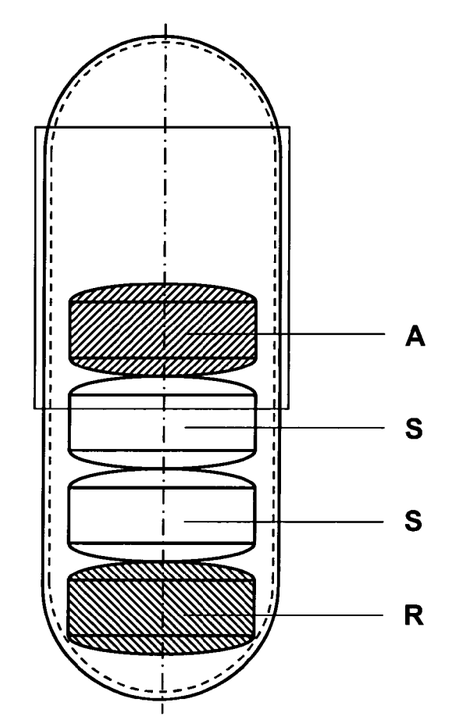
FIG. 1 shows a capsule representing the object of the present invention comprising 1 coated tablet comprising 100 mg of acetylsalicylic acid (A), 2 coated tablets each comprising 20 mg of simvastatin (S) and 1 coated tablet comprising 2.5 mg of ramipril (R).

The present invention relates to the manufacture of therapeutic combinations for the prevention of cardiovascular diseases comprising acetylsalicylic acid, HMG-CoA reductase inhibitors and ACE inhibitors at fixed doses that are adaptable to the doses required by individual patients or certain population subgroups.

Moreover, the compositions of the present invention have the advantage of preserving the active ingredients from degradation by light, as do capsules. This advantage is increased by the fact that the active ingredients are in turn present as coated tablets, a fact that prevents incompatibility between the different components. Based on the total weight of the tablet, the proportion of the coating is usually in the range of 1-12% w/w, preferably 2-6% w/w. The coating comprises a film-forming agent, such as a film-forming polymer, e.g. partially hydrolysed polyvinyl alcohol, hydroxypropylmethyl cellulose, or the like. The coating may comprise further conventional excipients.

In the course of the investigation it has been discovered that acetylsalicylic acid degrades to salicylic acid due to moisture. Subsequent acetylsalicylic acid sublimation occurs on the surface of ACE inhibitor tablets thus inducing its chemical degradation. A partially hydrolysed polyvinyl alcohol coating film (Opadry AMB™, Colorcon) has been found useful for protecting both acetylsalicylic acid and the ACE inhibitor tablets because of its moisture barrier properties. HMG-CoA reductase inhibitor tablets in the present invention may be coated with a coloured film, such as a hydroxypropylmethyl cellulose comprising film (Opadry Orange™, Colorcon) to hide darkened appearance. Opadry AMB coatings also may comprise one or more than one pigment.

As a result, the compositions of the present invention are safe, stable and effective and they are small in size, which allows them to be easily swallowed. According to one embodiment, they release the oral doses in a essentially immediate release format.

Finally, the evidence of toxicological safety together with the absence of pharmacodynamic and pharmacokinetic interactions, the benefits of the combined therapy of acetylsalicylic acid with HMG-CoA reductase inhibitors such as simvastatin and pravastatin, and with ACE inhibitors such as lisinopril, perindopril and ramipril, and the fact that the possible side effects are predictable, not serious and can be clinically controlled without great risk for the patients, allows the conclusion that the combinations of the present invention produce innovative, safe and effective treatments.

Simvastatin chemically corresponds to (4R,6R)-6-[2-[(1S,2S,6R,8S,8aR)-1,2,6,7,8,8a-hexahydro-8-hydroxy-2,6-dimethyl-1-naphthyl]ethyl]tetrahydro-4-hydroxy-2H-pyran-2-one 8-ester with 2,2-dimethylbutyric acid (WHO). Pravastatin chemically corresponds to (3R,5R)-7-{(1S,2S,6S,8S,8aR)-1,2,6,7,8,8a-hexahydro-6-hydroxy-2-methyl-8-[(S)-2-methylbutyryloxy]-1-naphthyl}-3,5-dihydroxy heptanoic acid (WHO). Lisinopril chemically corresponds to 1-[$N^2$-[(S)-1-carboxy-3-phenylpropyl]-L-lysyl]-L-proline (WHO). Ramipril chemically corresponds to the 1-ethylic ester of (2S,3aS,6aS)-1-[(S)-N-[(S)-1-carboxy-3-phenylpropyl]alanyl]octahydrocyclopenta[b]pyrrol-2-carboxylic acid (OMS). Perindopril chemically corresponds to the 1-ethylic ester of (2S,3aS,7aS)-1-[(S)-N-[(S)-1-carboxybutyl]alanyl] hexahydro-2-indolinecarboxylic acid (OMS).

The present invention relates to a capsule customized to the individual characteristics of each patient or subgroup of the population for the prevention of cardiovascular diseases characterised in that it comprises:
(i) a) w coated tablet(s) comprising 40.5 mg of acetylsalicylic acid and x coated tablet(s) comprising 81 mg of acetylsalicylic acid, wherein w is an integer chosen from 0 and 1, and x is an integer chosen from 0, 1 and 2, such that the total amount of acetylsalicylic acid is from 40.5 to 162 mg and w+x is 1 or 2; or
  b) y coated tablet(s) comprising 50 mg of acetylsalicylic acid and z coated tablet(s) comprising 100 mg of acetylsalicylic acid, wherein y is an integer chosen from 0 and 1, and z is an integer chosen from 0, 1 and 2, such that the total amount of acetylsalicylic acid is from 50 to 200 mg and y+z is 1 or 2;
(ii) a) s coated tablet(s) comprising 20 mg of simvastatin and t coated tablet(s) comprising 40 mg of simvastatin, wherein s is an integer chosen from 0, 1 and 2, and t is an integer chosen from 0, 1 and 2, such that the total amount of simvastatin is from 20 to 80 mg and s+t is 1 or 2; or
  b) u coated tablet(s) comprising 20 mg of pravastatin or a pharmaceutically acceptable salt thereof and v coated tablet(s) comprising 40 mg of pravastatin or a pharmaceutically acceptable salt thereof, wherein u is an integer chosen from 0, 1 and 2, and v is an integer chosen from 0, 1 and 2, such that the total amount of pravastatin or a pharmaceutically acceptable salt thereof is from 20 to 80 mg and u+v is 1 or 2; and
(iii) a) p coated tablet(s) comprising 5 mg of lisinopril or a hydrated form, q coated tablet(s) comprising 10 mg of lisinopril or a hydrated form and r coated tablet(s) comprising 20 mg of lisinopril or a hydrated form, wherein p is an integer chosen from 0 and 1, q is an integer chosen from 0 and 1, and r is an integer chosen from 0, 1 and 2, such that the total amount of lisinopril or hydrated form is from 5 to 40 mg and p+q+r is 1, 2 or 3; or
  b) k coated tablet(s) comprising 2.5 mg of ramipril, m coated tablet(s) comprising 5 mg of ramipril and n coated tablet(s) comprising 10 mg of ramipril, wherein k is an integer chosen from 0 and 1, m is an integer chosen from 0 and 1, and n is an integer chosen from 0, 1 and 2, such that the total amount of ramipril is from 2.5 to 20 mg and k+m+n is 1, 2 or 3; or
  c) h coated tablet(s) comprising 2 mg of perindopril or a pharmaceutically acceptable salt thereof, i coated tablet(s) comprising 4 mg of perindopril or a pharmaceutically acceptable salt thereof, and j coated tablet(s) comprising 8 mg of perindopril or a pharmaceutically acceptable salt thereof, wherein h is an integer chosen from 0 and 1, i is an integer chosen from 0 and 1, and j is an integer chosen from 0, 1 and 2, such that the total amount of perindopril or a pharmaceutically acceptable salt thereof is 2 to 16 mg and h+i+j is 1, 2 or 3;
wherein:
  the acetylsalicylic acid tablets are coated with a partially hydrolysed polyvinyl alcohol comprising film;
  the simvastatin tablets are coated with a hydroxypropylmethyl cellulose comprising film;
  the pravastatin or pharmaceutically acceptable salt tablets are coated with a hydroxypropylmethyl cellulose comprising film;
  the lisinopril or hydrated form tablets are coated with a partially hydrolysed polyvinyl alcohol comprising film;
  the ramipril tablets are coated with a partially hydrolysed polyvinyl alcohol comprising film; and
  the perindopril or pharmaceutically acceptable salt tablets are coated with a partially hydrolysed polyvinyl alcohol comprising film.

Preferred amongst the pharmaceutically acceptable salts of pravastatin are those from alkaline metals or alkaline earth metals. The most preferred salt is the sodium salt. Lisinopril usually occurs as a dihydrate, which is therefore the preferred form used in the present invention. Amongst the pharmaceutically acceptable salts of perindopril are alkaline salts and alkylamine salts, the most preferred being the salt with t-butylamine, also called erbumine salt.

According to a particular embodiment, all tablets have unmodified release format. As used herein the term "unmodified release" format is understood to be defined as pertaining to the dissolution and bioavailability profile of an active ingredient wherein no additional modifications, be it chemical or physical, have been made to the ingredient with the specific intent to alter the dissolution or bioavailability profile from that of ingredient in a usual form. It is also understood that unmodified release is, essentially, immediate release of active ingredients. This is further understood to be traditional or conventional release format where no slow, delayed or extended release effect is incorporated. Immediate release means that the tablets rapidly dissolve in vitro and in the stomach or upper gastrointestinal tract. Preferably, immediate release means that at least 80% of the active ingredient is released within 60 minutes, preferably within 30 minutes of administration. The test method is a dissolution test given in examples 6 which is used for simvastatin or pravastatin and in example 7 which is used for the ACE inhibitor.

In a preferred embodiment of the present invention, the capsules are characterised in that they comprise:
  (i) a) one coated tablet comprising 81 mg of acetylsalicylic acid; or
    b) one coated tablet comprising 100 mg of acetylsalicylic acid;
  (ii) a) two coated tablets each comprising 20 mg of simvastatin; or
    b) two coated tablets each comprising 20 mg of pravastatin sodium salt; and
  (iii) a) one coated tablet comprising 5, 10 or 20 mg of lisinopril dihydrate; or
    b) one coated tablet comprising 2.5, 5 or 10 mg of ramipril; or
    c) one coated tablet comprising 2, 4 or 8 mg of perindopril erbumine salt.

In a preferred embodiment of the present invention, the capsules are characterised in that they comprise:
(1) one coated tablet comprising 81 mg acetylsalicylic acid, two coated tablets each comprising 20 mg simvastatin and one coated tablet comprising 5 mg lisinopril dihydrate;
(2) one coated tablet comprising 81 mg acetylsalicylic acid, two coated tablets each comprising 20 mg simvastatin and one coated tablet comprising 10 mg lisinopril dihydrate;
(3) one coated tablet comprising 81 mg acetylsalicylic acid, two coated tablets each comprising 20 mg simvastatin and one coated tablet comprising 20 mg lisinopril dihydrate;
(4) one coated tablet comprising 81 mg acetylsalicylic acid, two coated tablets each comprising 20 mg simvastatin and one coated tablet comprising 2.5 mg ramipril;
(5) one coated tablet comprising 81 mg acetylsalicylic acid, two coated tablets each comprising 20 mg simvastatin and one coated tablet comprising 5 mg ramipril;
(6) one coated tablet comprising 81 mg acetylsalicylic acid, two coated tablets each comprising 20 mg simvastatin and one coated tablet comprising 10 mg ramipril;
(7) one coated tablet comprising 81 mg acetylsalicylic acid, two coated tablets each comprising 20 mg simvastatin and one coated tablet comprising 2 mg perindopril erbumine;
(8) one coated tablet comprising 81 mg acetylsalicylic acid, two coated tablets each comprising 20 mg simvastatin and one coated tablet comprising 4 mg perindopril erbumine;
(9) one coated tablet comprising 81 mg acetylsalicylic acid, two coated tablets each comprising 20 mg simvastatin and one coated tablet comprising 8 mg perindopril erbumine;

(10) one coated tablet comprising 81 mg acetylsalicylic acid, two coated tablets each comprising 20 mg pravastatin sodium salt and one coated tablet comprising 5 mg lisinopril dihydrate;
(11) one coated tablet comprising 81 mg acetylsalicylic acid, two coated tablets each comprising 20 mg pravastatin sodium salt and one coated tablet comprising 10 mg lisinopril dihydrate;
(12) one coated tablet comprising 81 mg acetylsalicylic acid, two coated tablets each comprising 20 mg pravastatin sodium salt and one coated tablet comprising 20 mg lisinopril dihydrate;
(13) one coated tablet comprising 81 mg acetylsalicylic acid, two coated tablets each comprising 20 mg pravastatin sodium salt and one coated tablet comprising 2.5 mg ramipril;
(14) one coated tablet comprising 81 mg acetylsalicylic acid, two coated tablets each comprising 20 mg pravastatin sodium salt and one coated tablet comprising 5 mg ramipril;
(15) one coated tablet comprising 81 mg acetylsalicylic acid, two coated tablets each comprising 20 mg pravastatin sodium salt and one coated tablet comprising 10 mg ramipril;
(16) one coated tablet comprising 81 mg acetylsalicylic acid, two coated tablets each comprising 20 mg pravastatin sodium salt and one coated tablet comprising 2 mg perindopril erbumine;
(17) one coated tablet comprising 81 mg acetylsalicylic acid, two coated tablets each comprising 20 mg pravastatin sodium salt and one coated tablet comprising 4 mg perindopril erbumine;
(18) one coated tablet comprising 81 mg acetylsalicylic acid, two coated tablets each comprising 20 mg pravastatin sodium salt and one coated tablet comprising 8 mg perindopril erbumine;
(19) one coated tablet comprising 100 mg acetylsalicylic acid, two coated tablets each comprising 20 mg simvastatin and one coated tablet comprising 5 mg lisinopril dihydrate;
(20) one coated tablet comprising 100 mg acetylsalicylic acid, two coated tablets each comprising 20 mg simvastatin and one coated tablet comprising 10 mg lisinopril dihydrate;
(21) one coated tablet comprising 100 mg acetylsalicylic acid, two coated tablets each comprising 20 mg simvastatin and one coated tablet comprising 20 mg lisinopril dihydrate;
(22) one coated tablet comprising 100 mg acetylsalicylic acid, two coated tablets each comprising 20 mg simvastatin and one coated tablet comprising 2.5 mg ramipril;
(23) one coated tablet comprising 100 mg acetylsalicylic acid, two coated tablets each comprising 20 mg simvastatin and one coated tablet comprising 5 mg ramipril;
(24) one coated tablet comprising 100 mg acetylsalicylic acid, two coated tablets each comprising 20 mg simvastatin and one coated tablet comprising 10 mg ramipril;
(25) one coated tablet comprising 100 mg acetylsalicylic acid, two coated tablets each comprising 20 mg simvastatin and one coated tablet comprising 2 mg perindopril erbumine;
(26) one coated tablet comprising 100 mg acetylsalicylic acid, two coated tablets each comprising 20 mg simvastatin and one coated tablet comprising 4 mg perindopril erbumine;
(27) one coated tablet comprising 100 mg acetylsalicylic acid, two coated tablets each comprising 20 mg simvastatin and one coated tablet comprising 8 mg perindopril erbumine;
(28) one coated tablet comprising 100 mg acetylsalicylic acid, two coated tablets each comprising 20 mg pravastatin sodium salt and one coated tablet comprising 5 mg lisinopril dihydrate;
(29) one coated tablet comprising 100 mg acetylsalicylic acid, two coated tablets each comprising 20 mg pravastatin sodium salt and one coated tablet comprising 10 mg lisinopril dihydrate;
(30) one coated tablet comprising 100 mg acetylsalicylic acid, two coated tablets each comprising 20 mg pravastatin sodium salt and one coated tablet comprising 20 mg lisinopril dihydrate;
(31) one coated tablet comprising 100 mg acetylsalicylic acid, two coated tablets each comprising 20 mg pravastatin sodium salt and one coated tablet comprising 2.5 mg ramipril;
(32) one coated tablet comprising 100 mg acetylsalicylic acid, two coated tablets each comprising 20 mg pravastatin sodium salt and one coated tablet comprising 5 mg ramipril;
(33) one coated tablet comprising 100 mg acetylsalicylic acid, two coated tablets each comprising 20 mg pravastatin sodium salt and one coated tablet comprising 10 mg ramipril;
(34) one coated tablet comprising 100 mg acetylsalicylic acid, two coated tablets each comprising 20 mg pravastatin sodium salt and one coated tablet comprising 2 mg perindopril erbumine;
(35) one coated tablet comprising, 100 mg acetylsalicylic acid two coated tablets each comprising 20 mg pravastatin sodium salt and one coated tablet comprising 4 mg perindopril erbumine; and
(36) one coated tablet comprising 100 mg acetylsalicylic acid, two coated tablets each comprising 20 mg pravastatin sodium salt and one coated tablet comprising 8 mg perindopril erbumine.

In the subsequent preferred embodiments of the present invention, the capsules are characterised in that they are made of hard gelatine.

In other subsequent preferred embodiments of the present invention, the capsules are characterised in that they are made of cellulose.

According to a particular embodiment, the capsules or tablets do not contain a further active compound, i.e. the capsules consist of components i), ii) and iii).

In a preferred embodiment of the present invention, the capsules are used for the prevention of cardiovascular diseases in high-risk populations, preferably in human subjects of more than 55 years of age, patients with a background of angor pectoris, ictus, arteriosclerosis, intermittent claudication, diabetes, coronary disease, peripheral vascular disease, altered platelet function, haemodialysis, hypercholesterolaemia, hypertension, myocardial infarction, congestive heart failure, ischaemia, nephropathy, cardisc arrest or restenosis, smokers, obese subjects and sedentary subjects.

The capsules of the present invention allow easy dose scaling by arithmetic progression at the physician's discretion by the minimum number of tablets per capsule and based on the characteristics of each patient or population subgroup to be treated. Acetylsalicylic acid doses have been determined based on the American standard of 81 mg (St. Joseph 81 mg Aspirin®) and the international standard of 100 mg. The scaling of possible doses is shown in Table 1.

TABLE 1

Dose scaling

Acetylsalicylic acid (40.5-162 mg, 50-200 mg; 40.5, 50 mg scaling)

|  |  |  |  |  |
|---|---|---|---|---|
| w, 40.5 mg | 1 | 0 | 1 | 0 |
| x, 81 mg | 0 | 1 | 1 | 2 |
| Total | 40.5 mg | 81 mg | 121.5 mg | 162 mg |
| y, 50 mg | 1 | 0 | 1 | 0 |
| z, 100 mg | 0 | 1 | 1 | 2 |
| Total | 50 mg | 100 mg | 150 mg | 200 mg |

HMG-CoA reductase inhibitors (20-80 mg, 20 mg scaling)
Simvastatin

|  |  |  |  |  |
|---|---|---|---|---|
| s, 20 mg | 1 | 0 | 1 | 0 |
| t, 40 mg | 0 | 1 | 1 | 2 |
| Total | 20 mg | 40 mg | 60 mg | 80 mg |

Pravastatin Sodium salt

|  |  |  |  |  |
|---|---|---|---|---|
| u, 20 mg | 1 | 0 | 1 | 0 |
| v, 40 mg | 0 | 1 | 1 | 2 |
| Total | 20 mg | 40 mg | 60 mg | 80 mg |

ACE inhibitors
Lisinopril dihydrate (5-40 mg, 5 mg scaling)

|  |  |  |  |  |  |  |  |  |
|---|---|---|---|---|---|---|---|---|
| p, 5 mg | 1 | 0 | 1 | 0 | 1 | 0 | 1 | 0 |
| q, 10 mg | 0 | 1 | 1 | 0 | 0 | 1 | 1 | 0 |
| r, 20 mg | 0 | 0 | 0 | 1 | 1 | 1 | 1 | 2 |
| Total | 5 mg | 10 mg | 15 mg | 20 mg | 25 mg | 30 mg | 35 mg | 40 mg |

Ramipril (2.5-20 mg, 2.5 mg scaling)

|  |  |  |  |  |  |  |  |  |
|---|---|---|---|---|---|---|---|---|
| k, 2.5 mg | 1 | 0 | 1 | 0 | 1 | 0 | 1 | 0 |
| m, 5 mg | 0 | 1 | 1 | 0 | 0 | 1 | 1 | 0 |
| n, 10 mg | 0 | 0 | 0 | 1 | 1 | 1 | 1 | 2 |
| Total | 2.5 mg | 5 mg | 7.5 mg | 10 mg | 12.5 mg | 15 mg | 17.5 mg | 20 mg |

Perindopril erbumine salt (2-16 mg, 2 mg scaling)

|  |  |  |  |  |  |  |  |  |
|---|---|---|---|---|---|---|---|---|
| h, 2 mg | 1 | 0 | 1 | 0 | 1 | 0 | 1 | 0 |
| i, 4 mg | 0 | 1 | 1 | 0 | 0 | 1 | 1 | 0 |
| j, 8 mg | 0 | 0 | 0 | 1 | 1 | 1 | 1 | 2 |
| Total | 2 mg | 4 mg | 6 mg | 8 mg | 10 mg | 12 mg | 14 mg | 16 mg |

The capsules of the present invention may be of various materials, the most common of these being conventional hard gelatine capsules and cellulose capsules. Amongst the cellulose capsules we include, without this implying a limitation, those formed by various alkylcelluloses, such as methylcellulose, carboxymethyl cellulose, hydroxypropyl cellulose and the preferred hydroxypropylmethyl cellulose (HPMC).

Thus, in a practical embodiment the present invention relates to both hard gelatine capsules (0.12-1.66% of iron oxides, expressed as black iron oxide or red iron oxide, or mixtures thereof; 0.37-2.33% of titanium dioxide; and 100% gelatine q.s.) and cellulose capsules (99% HPMC; 0.2% of carrageenan; 0.15% of potassium chloride; and 0.65% pigments). The compositions of both the hard gelatine capsules and the cellulose capsules are not intended to imply limitations of the scope of the invention.

The tablets usually comprise pharmaceutically acceptable excipients such as diluents, binding agents, disintegrants, lubricants, glidants, antioxidants, pH regulators and film-forming polymers and the like.

Amongst the diluents we can name, without this necessarily implying a limiting nature, calcium phosphate, dicalcium phosphate, tricalcium phosphate, calcium sulphate, microcrystalline cellulose, kaolin, bentonite, starch, magnesium carbonate, several saccharides such as mannitol, lactose, either anhydrous, spraydried or wet, sorbitol, sucrose, inositol, compressible sugar, trehalose, xylitol, and the like, and mixtures thereof.

Amongst the binders we can name, without this necessarily implying a limiting nature, acacia, microcrystalline cellulose, cellulosic solutions such as HPMC, 10-20% gelatine solutions, 20-50% glucose solutions, polyvinylpyrrolidone, 10-20% starch paste, sorbitol, tragacanth, polyethylene glycol, maltodextrin, polymethacrylates and the like, and mixtures thereof.

Amongst the disintegrants we can mention, without this necessarily implying a limiting nature, corn and potato starch, methylcellulose, cellulose in general, calcium carboxymethylcellulose, mineral clay powder such as bentonite/veegum, wetting agents such as sodium lauryl sulphate, super-disintegrants, so called due to the low concentration they are used at (typically 2-4%), such as croscarmellose, crospovidone, sodium starch glycolate and the like, and mixtures thereof.

Amongst the lubricants we can mention, without this necessarily implying a limiting nature, polyethylene glycol, poloxamer, magnesium stearate, calcium stearate, stearic acid, hydrogenated vegetable oils, talc, glyceryl behenate and the like, and mixtures thereof.

Amongst the glidants we can mention, without this necessarily implying a limiting nature, colloidal silica (1%), talc, sodium stearyl fumarate, corn starch and the like, and mixtures thereof.

Amongst the antioxidants we can mention, without this necessarily implying a limiting nature, butylated hydroxyanisole, butylated hydroxytoluene, ascorbic acid, sodium ascorbate, propyl gallate, sodium or potassium metabisulphite, fumaric acid and the like, and mixtures thereof.

Amongst the pH regulators we can mention, without this necessarily implying a limiting nature, sodium bicarbonate, magnesium oxide, calcium phosphate, citric acid, potassium citrate and the like, and mixtures thereof.

Amongst the film-forming polymers we can mention, without this necessarily implying a limiting nature, polyvinyl acetate phthalate, certain cellulose derivatives such as cellulose acetate, HPMC, ethylcellulose, methylcellulose acetate succinate, polymethacrylates, methacrylic acid copolymers, methylcellulose acetate succinate, polyvinyl alcohol and the like, and mixtures thereof.

Embodiments of the Invention

The present invention is additionally illustrated by means of the following examples, which do not intent to limit the scope thereof.

Example 1

Hard gelatine capsules containing one coated tablet comprising 100 mg acetylsalicylic acid, two coated tablets comprising 20 mg simvastatin and one coated tablet comprising 2.5, 5 or 10 mg ramipril.

a) Manufacture of the Acetylsalicylic Acid-Coated Tablets

They were manufactured according to the usual procedures in the industry, according to the following sequential procedure. The acetylsalicylic acid, sodium starch glycolate and microcrystalline cellulose 101 were sieved in the appropriate proportions, the three components were mixed, the previously sieved talc was then added, it was mixed again, compressed and the resulting core was coated with an Opadry AMB white OY-B-28920 aqueous film-forming solution. Coated tablets were thus obtained with 100 mg of acetylsalicylic acid, the composition of which is shown in Table 2. The composition of the Opadry AMB white OY-B-28920 coating agent is shown in Table 3. The ingredients for preparing the Opadry AMB white OY-B-28920 aqueous solution corresponding to 1 coated tablet of 100 mg of acetylsalicylic acid are shown in Table 4.

TABLE 2

Coated tablets, 100 mg of acetylsalicylic acid

| Core | Components | Acetylsalicylic acid | 100.000 mg |
|---|---|---|---|
| | | Microcrystalline cellulose 101 | 20.000 mg |
| | | Sodium starch glycolate | 3.750 mg |
| | | Talc | 1.250 mg |
| | Core total | | 125.000 mg |
| Coating | Opadry AMB white OY-B-28920 | | 6.250 mg |
| Total coated tablet | | | 131.250 mg |

TABLE 3

Opadry AMB white OY-B-28920

| Partially hydrolysed polyvinyl alcohol | 45.50% |
|---|---|
| Titanium dioxide | 32.00% |
| Talc | 20.00% |
| Soy lecithin | 2.00% |
| Xanthan gum | 0.50% |
| Total | 100.00% |

TABLE 4

Ingredients for preparing the aqueous solution of Opadry AMB white OY-B-28920 corresponding to 1 coated tablet of 100 mg of acetyl-salicylic acid

| Opadry AMB white OY-B-28920 | 6.250 mg |
|---|---|
| Purified water | 56.250 mg | b) Manufacture of the Coated Tablets Comprising 20 mg of Simvastatin

They were manufactured according to the usual procedures in the industry, according to the following sequential procedure. The micronized simvastatin, lactose monohydrate, pregelatinized starch 1500, ascorbic acid and citric acid were sieved in the appropriate proportions, said components were mixed, purified water was added, it was dried and sieved, thus obtaining Sieving 1. On the other hand, butylated hydroxyanisole (BHA) was prepared as granules at 0.4%. This was achieved from microcrystalline cellulose 102, which was sieved, mixed with an ethanol solution of BHA, which was then dried and sieved, thus obtaining BHA as granules at 0.4%. In turn, a mixture was prepared consisting of microcrystalline cellulose 102, the 0.4% BHA granules, colloidal anhydrous silica, talc and magnesium stearate, which was then sieved to obtain Sieving 2. Sieving 1 and Sieving 2 were mixed and compressed and the resulting core was coated with an Opadry orange 06023821 aqueous film-forming solution. Coated tablets with 20 mg of simvastatin were thus obtained the composition of which is shown in Table 5. The composition of the Opadry orange 06023821 coating agent is shown in Table 6. The ingredients for preparing the 0.4% BHA granules corresponding to 1 coated tablet of 20 mg of simvastatin are shown in Table 7. The ingredients for preparing Sieving 1 corresponding to 1 coated tablet of 20 mg of simvastatin are shown in Table 8. The ingredients for preparing the Opadry orange 06023821 aqueous solution corresponding to 1 coated tablet of 20 mg of simvastatin are shown in Table 9.

TABLE 5

Coated tablets, 20 mg of simvastatin

| Core | Components | Micronized simvastatin | 20.000 mg |
|---|---|---|---|
| | | Lactose monohydrate | 45.000 mg |
| | | Pregelatinised starch 1500 | 10.000 mg |
| | | Ascorbic acid | 5.000 mg |
| | | Citric acid | 2.500 mg |
| | | Microcrystalline cellulose 102 | 11.960 mg |
| | | Butylated hydroxyanisole | 0.040 mg |
| | | Colloidal anhydrous silica | 0.500 mg |
| | | Talc | 4.000 mg |
| | | Magnesium stearate | 1.000 mg |
| | Core total | | 100.000 mg |
| Coating | Opadry orange 06023821 | | 3.000 mg |
| Total coated tablet | | | 103.000 mg |

TABLE 6

Opacity orange 06023821

| Hypromellose 606 | 37.80% |
|---|---|
| Hypromellose E15LVP | 12.59% |
| Red iron oxide | 0.19% |
| Yellow iron oxide | 0.77% |
| Triethyl citrate | 8.14% |
| Titanium dioxide | 4.72% |
| Talc | 33.27% |
| Povidone K30 | 2.52% |
| Total | 100.00% |

TABLE 7

Ingredients for preparing the 0.4% BHA granules corresponding to 1 coated tablet comprising 20 mg of simvastatin

| | |
|---|---|
| Microcrystalline cellulose 102 | 10.000 mg |
| Butylated hydroxyanisole | 0.040 mg |
| 96° Ethanol | 3.750 mg |

TABLE 8

Ingredients for preparing Sieving 1 corresponding to 1 coated tablet comprising 20 mg of simvastatin

| | |
|---|---|
| Micronized simvastatin | 20.000 mg |
| Lactose monohydrate | 45.000 mg |
| Pregelatinised starch 1500 | 10.000 mg |
| Ascorbic acid | 5.000 mg |
| Citric acid | 2.500 mg |
| Purified water | 17.000 mg |

TABLE 9

Ingredients for preparing the aqueous solution of Opadry orange 06023821 corresponding to 1 coated tablet comprising 20 mg of simvastatin

| | |
|---|---|
| Opadry orange 06023821 | 3.000 mg |
| Purified water | 27.000 mg | c) Manufacture of Coated Tablets Comprising 2.5, 5 and 10 mg of Ramipril

They were manufactured according to the usual procedures in the industry, according to the following sequential procedure. The ramipril, sodium bicarbonate and pregelatinized starch 1500 were dry sieved and mixed in the appropriate proportions. The previously sieved microcrystalline cellulose 101 was added in two steps (premix and second mixture), being dry-mixed after each addition. HPMC was added into purified water, followed by mixing, drying and sieving, thus obtaining Sieving 1. Previously sieved microcrystalline cellulose 101 was added, mixed, previously sieved sodium stearyl fumarate was added, it was mixed, compressed, and the resulting core was coated with an Opadry AMB yellow aqueous film-forming solution. Coated tablets of 2.5, 5 and 10 mg of ramipril were thus obtained the compositions of which are shown respectively in Tables 10, 11 and 12. The breaking strength of the tablets obtained was 9-11 kp their disintegration time was 0.5-2 min. The composition of the Opadry AMB yellow coating agent is shown in Tables 13, 14 and 15, corresponding respectively to the coated tablets of 2.5, 5 and 10 mg of ramipril. The ingredients for preparing Sieving 1 corresponding to 1 coated tablet of 2.5, 5 and 10 mg of ramipril are shown respectively in Tables 16, 17 and 18. The ingredients for preparing the Opadry AMB yellow aqueous solution corresponding to 1 coated tablet of 2.5, 5 or 10 mg of ramipril are shown in Table 19.

TABLE 10

Coated tablet, 2.5 mg of ramipril

| | | | |
|---|---|---|---|
| Core | Components | Ramipril | 2.500 mg |
| | | HPMC | 0.500 mg |
| | | Sodium bicarbonate | 1.000 mg |
| | | Pregelatinised starch 1500 | 10.000 mg |
| | | Microcrystalline cellulose 101 | 86.200 mg |
| | | Sodium stearyl fumarate | 0.800 mg |
| | Core total | | 101.000 mg |
| Coating | Opadry AMB yellow 80W32039 | | 4.000 mg |
| Total coated tablet | | | 105.000 mg |

TABLE 11

Coated tablet, 5 mg of ramipril

| | | | |
|---|---|---|---|
| Core | Components | Ramipril | 5.000 mg |
| | | HPMC | 0.500 mg |
| | | Sodium bicarbonate | 2.000 mg |
| | | Pregelatinised starch 1500 | 10.000 mg |
| | | Microcrystalline cellulose 101 | 82.700 mg |
| | | Sodium stearyl fumarate | 0.800 mg |
| | Core total | | 101.000 mg |
| Coating | Opadry AMB yellow 80W32656 | | 4.000 mg |
| Total coated tablet | | | 105.000 mg |

TABLE 12

Coated tablet, 10 mg of ramipril

| | | | |
|---|---|---|---|
| Core | Components | Ramipril | 10.000 mg |
| | | HPMC | 0.500 mg |
| | | Sodium bicarbonate | 4.000 mg |
| | | Pregelatinised starch 1500 | 10.000 mg |
| | | Microcrystalline cellulose 101 | 75.700 mg |
| | | Sodium stearyl fumarate | 0.8000 mg |
| | Core total | | 101.000 mg |
| Coating | Opadry AMB yellow 80W32880 | | 4.000 mg |
| Total coated tablet | | | 105.000 mg |

TABLE 13

Opadry AMB yellow 80W32039 for 2 coated tablets comprising 5 mg of ramipril

| | |
|---|---|
| Partially hydrolysed polyvinyl alcohol | 45.52% |
| Titanium dioxide | 30.70% |
| Talc | 20.00% |
| Soy lecithin | 2.00% |
| Yellow iron oxide | 1.30% |
| Xanthan gum | 0.48% |
| Total | 100.00% |

TABLE 14

Opadry AMB yellow 80W32656 for coated tablets comprising 5 mg of ramipril

| | |
|---|---|
| Partially hydrolysed polyvinyl alcohol | 45.52% |
| Titanium dioxide | 29.61% |
| Talc | 20.00% |
| Soy lecithin | 2.39% |
| Yellow iron oxide | 2.00% |
| Xanthan gum | 0.48% |
| Total | 100.00% |

TABLE 15

Opadry AMB yellow 80W32880 for coated tablets comprising 10 mg of ramipril

| | |
|---|---|
| Partially hydrolysed polyvinyl alcohol | 45.52% |
| Titanium dioxide | 27.20% |
| Talc | 20.00% |
| Soy lecithin | 4.80% |
| Yellow iron oxide | 2.00% |
| Xanthan gum | 0.48% |
| Total | 100.00% |

TABLE 16

Ingredients for preparing Sieving 1 corresponding to 1 coated tablet comprising 2.5 mg of ramipril

| | |
|---|---|
| Ramipril | 2.500 mg |
| HPMC | 0.500 mg |
| Sodium bicarbonate | 1.000 mg |
| Pregelatinised starch 1500 | 10.000 mg |
| Microcrystalline cellulose 101 (premix) | 32.000 mg |
| Microcrystalline cellulose 101 (second mixture) | 25.000 mg |
| Purified water | 45.000 mg |

TABLE 17

Ingredients for preparing Sieving 1 corresponding to 1 coated tablet comprising 5 mg of ramipril

| | |
|---|---|
| Ramipril | 5.000 mg |
| HPMC | 0.500 mg |
| Sodium bicarbonate | 2.000 mg |
| Pregelatinised starch 1500 | 10.000 mg |
| Microcrystalline cellulose 101 (premix) | 28.500 mg |
| Microcrystalline cellulose 101 (second mixture) | 25.000 mg |
| Purified water | 40.000 mg |

TABLE 18

Ingredients for preparing Sieving 1 corresponding to 1 coated tablet comprising 10 mg of ramipril

| | |
|---|---|
| Ramipril | 10.000 mg |
| HPMC | 0.500 mg |
| Sodium bicarbonate | 4.000 mg |
| Pregelatinised starch 1500 | 10.000 mg |
| Microcrystalline cellulose 101 (premix) | 21.500 mg |
| Microcrystalline cellulose 101 (second mixture) | 25.000 mg |
| Purified water | 35.000 mg |

TABLE 19

Ingredients for preparing the Opadry AMB yellow aqueous solution corresponding to 1 coated tablet comprising 2.5, 5 or 10 mg of ramipril

| | |
|---|---|
| Opadry AMB yellow | 4.000 mg |
| Purified water | 36.000 mg | d) Encapsulating Procedure

The coated tablets of ramipril, simvastatin and acetylsalicylic acid were introduced in a proportion of 1:2:1 respectively, in #0 size hard gelatine capsules using an ordinary encapsulating machine for this purpose. Three different filling hoppers were enabled to this end, one for each type of tablet. The capsules were filled with the aid of a punch that pushed the tablets into the capsule, the machine being provided with a quality assurance system prepared to reject capsules with an incorrect number of tablets.

e) Stability Study

Each of the batches of capsules obtained in a-d) packaged in an aluminium/aluminium (Alu/Alu) blister and in a PVC/PVDC (polyvinyl chloride/polyvinyl dichloride)-aluminium blister were subjected to variables conditions of temperature and relative humidity (rh) for 3 months, the following results being obtained on the impurities or degradation products found in the various conditions.

1. Stability of the Acetylsalicylic Acid Tablets

| Start | | |
|---|---|---|
| Salicylic acid | Other impurities | Total impurities |
| 0.60% | Undetected | 0.60% |

| | | 3 months | | |
|---|---|---|---|---|
| Conditions | Batch | Salicylic acid | Other impurities | Total impurities |
| 25° C. 60% rh | Alu/Alu | 0.35% | Undetected | 0.4% |
| | PVC/PVDC | 0.34% | Undetected | 0.4% |
| 30° C. 65% rh | Alu/Alu | 1.43% | Undetected | 1.4% |
| | PVC/PVDC | 0.56% | Undetected | 0.6% |
| 40° C. 75% rh | Alu/Alu | 0.76% | Undetected | 0.8% |
| | PVC/PVDC | 1.76% | Undetected | 1.8% |

2. Stability of the Simvastatin Tablets

| Start | | | | |
|---|---|---|---|---|
| Lovastatin | Impurity A | Impurity C | Other impurities | Total impurities |
| Undetected | 0.11% | Undetected | 0.06% | 0.17% |

Impurity A = simvastatin hydroxy acid
Impurity C = anhydrosimvastatin

| | | 3 months | | | | |
|---|---|---|---|---|---|---|
| Conditions | Batch | L(1) | Impurity A | Impurity C | Other impurities | Total impurities |
| 25° C. 60% rh | Alu/Alu | 0.02% | 0.28% | n.d. (2) | 0.05% | 0.43% |
| | PVC/PVDC | 0.02% | 0.31% | n.d. (2) | 0.05% | 0.47% |
| 30° C. 65% rh | Alu/Alu | 0.02% | 0.22% | 0.02% | 0.29% | 0.63% |
| | PVC/PVDC | 0.02% | 0.26% | 0.02% | 0.31% | 0.69% |

3. Stability of the Ramipril Tablets

-continued

| | | | 3 months | | | |
|---|---|---|---|---|---|---|
| Conditions | Batch | L(1) | Impurity A | Impurity C | Other impurities | Total impurities |
| 40° C. 75% rh | Alu/Alu | 0.02% | 0.21% | 0.06% | 1.13% | 1.50% |
| | PVC/PVDC | 0.02% | 0.36% | 0.12% | 1.69% | 2.31% |

(1) lovastatin
(2) undetected

| Start | | |
|---|---|---|
| Impurity D | Unknown impurities | Total impurities |
| 0.04% | 0.05% | 0.21% |

Impurity D = ramipril diketopiperazine

| | | | 3 months | | | |
|---|---|---|---|---|---|---|
| Conditions | Batch | BHA | AA (1) | Impurity D | Impurity E | Total impurities |
| 25° C. 60% rh | Alu/Alu | n.d. (2) | n.d. (2) | 0.1% | 0.1% | <0.1% |
| | PVC/PVDC | n.d. (2) | n.d. (2) | 0.1% | 0.1% | n.d. (3) |
| 30° C. 65% rh | Alu/Alu | n.d. (2) | n.d. (2) | 0.1% | 0.1% | 0.1% |
| | PVC/PVDC | n.d. (2) | n.d. (2) | 0.1% | 0.2% | <0.1% |
| 40° C. 75% rh | Alu/Alu | 0.2% | 0.1% | 0.1% | 0.2% | n.d. (3) |
| | PVC/PVDC | 1.1% | n.d. (2) | 0.4% | 0.7% | 0.2% |

(1) acetylsalicylic acid
(2) undetected
(3) undetected
Impurity E = ramipril diacid

Example 2

Hard gelatine capsules containing one coated tablet comprising 100 mg acetylsalicylic acid, two coated tablets comprising 20 mg simvastatin and one coated tablet comprising 10 mg ramipril.

Similarly to example 1, the title capsules were prepared in which the only difference was the composition of the ramipril tablet, which is shown in Table 20. Tablet breaking strength was 9-11 kp and disintegration time 1-2 min.

TABLE 20

| Coated tablet of 10 mg ramipril | | | |
|---|---|---|---|
| Core | Components | Ramipril | 10.000 mg |
| | | HPMC | 1.000 mg |
| | | Pregelatinised starch 1500 | 8.000 mg |
| | | Microcrystalline cellulose 101 | 78.200 mg |
| | | Sodium starch glycolate | 2.000 mg |
| | | Sodium stearyl fumarate | 800 mg |
| | Core total | | 100.000 mg |
| Coating | Opadry AMB yellow 80W32880 | | 4.000 mg |
| Total coated tablet | | | 104.000 mg |

Example 3

Hard gelatine capsules containing one coated tablet comprising 100 mg acetylsalicylic acid, two coated tablets comprising 20 mg simvastatin and one coated tablet comprising 20 mg lisinopril dihydrate.

Similarly to example 1, the title capsules were prepared in which the only difference was the composition of the lisinopril dihydrate tablet, which is shown in Table 21. Tablet breaking strength was 5.5-7.5 kp and disintegration time<1 min.

TABLE 21

| Coated tablet, 20 mg of lisinopril dihydrate | | | |
|---|---|---|---|
| Core | Components | Lisinopril dihydrate | 20.000 mg |
| | | Corn starch | 5.000 mg |
| | | Pregelatinised starch 1500 | 5.000 mg |
| | | Mannitol | 25.000 mg |
| | | Calcium phosphate dihydrate | 44.500 mg |
| | | Magnesium stearate | 500 mg |
| | Core total | | 100.000 mg |
| Coating | Opadry AMB yellow 80W32039 | | 4.000 mg |
| Total coated tablet | | | 104.000 mg |

Example 4

Hard gelatine capsules containing one coated tablet comprising 100 mg acetylsalicylic acid, two coated tablets comprising 20 mg simvastatin and one coated tablet comprising 10 mg ramipril.

Similarly to example 1, the title capsules were prepared in which the only difference was the composition of the ramipril tablet, which is shown in Table 22. Tablet breaking strength was 9-11 kp and disintegration time 0.5-2 min.

TABLE 22

| | | Coated tablet, 10 mg of ramipril | |
|---|---|---|---|
| Core | Components | Ramipril | 10.000 mg |
| | | Pregelatinised starch 1500 | 10.000 mg |
| | | Microcrystalline cellulose 101 | 79.200 mg |
| | | Sodium stearyl fumarate | 800 mg |
| | Core total | | 100.000 mg |
| Coating | Opadry AMB yellow 80W32880 | | 4.000 mg |
| Total coated tablet | | | 104.000 mg |

Example 5

Hard gelatine capsules containing one coated tablet comprising 100 mg acetylsalicylic acid, two coated tablets comprising 20 mg simvastatin and one coated tablet comprising 10 mg ramipril.

Similarly to example 1, the title capsules were prepared in which the only difference was the composition of the simvastatin tablet, which is shown in Table 23.

TABLE 23

| | | Coated tablets, 20 mg of simvastatin | |
|---|---|---|---|
| Core | Components | Micronized simvastatin | 20.000 mg |
| | | Lactose monohydrate | 51.960 mg |
| | | Pregelatinized starch 1500 | 10.000 mg |
| | | Ascorbic acid | 5.000 mg |
| | | Citric acid | 2.500 mg |
| | | Microcrystalline cellulose 101 | 5.000 mg |
| | | Butylated hydroxyanisole | 0.040 mg |
| | | Colloidal anhydrous silica | 0.500 mg |
| | | Talc | 4.000 mg |
| | | Magnesium stearate | 1.000 mg |
| | Core total | | 100.000 mg |
| Coating | Opadry orange 06023821 | | 3.000 mg |
| Total coated tablet | | | 103.000 mg |

Example 6

Dissolution Test for the Simvastatin Tablets

The dissolution test was performed on the simvastatin tablets of example 4. To this end 1 simvastatin tablet was introduced per capsule using size #0 hard gelatine and cellulose capsules, in a buffered aqueous medium at pH 7 and containing 0.5% sodium dodecyl sulphate in 0.01 N sodium phosphate, at 37° C. The results obtained are those of Table 24.

TABLE 24

| Dissolution test for the simvastatin tablets | | |
|---|---|---|
| | Capsules | |
| Time (min) | Hard gelatine | Cellulose |
| 5 | 18.78 ± 47.39% | 0.00% |
| 15 | 69.69 ± 13.98% | 57.17 ± 15.02% |
| 30 | 85.05 ± 7.36% | 90.31 ± 3.95% |

Example 7

Dissolution Test for the Ramipril Tablets 1 ramipril tablet from example 4 was introduced per capsule using size #0 hard gelatine and cellulose capsules in an aqueous solution of 0.1 N HCl at 37° C. The results obtained are those of Table 25.

TABLE 25

| Dissolution test for the ramipril tablets | | |
|---|---|---|
| | Capsules | |
| Time (min) | Hard gelatine | Cellulose |
| 5 | 86.29 ± 2.41% | 6.93 ± 83.65% |
| 15 | 90.17 ± 1.93% | 84.68 ± 2.65% |
| 30 | 91.22 ± 1.80% | 89.49 ± 2.37% |

Example 8

Dissolution Test for the Acetylsalicylic Acid Tablets 1 acetylsalicylic acid tablet from example 4 was introduced in a buffered aqueous medium at pH 4.5, at 37° C. The results obtained are those of Table 26.

TABLE 26

| Dissolution test for the acetylsalicylic tablets | |
|---|---|
| 0 min | 0% |
| 5 min | 40% |
| 15 min | 90% |
| 30 min | 96% |

Example 9

Hard gelatine capsules containing one coated tablet comprising 100 mg acetylsalicylic acid, two coated tablets comprising 20 mg simvastatin and one coated tablet comprising 2.5, 5 or 10 mg ramipril.

Similarly to example 1, the title capsules were prepared in which the only difference was the composition of the ramipril tablets, which are shown in Tables 27, 28 and 29, corresponding respectively to the coated tablets of 2.5, 5 and 10 mg of ramipril.

TABLE 27

| | | Coated tablet, 2.5 mg of ramipril | |
|---|---|---|---|
| Core | Components | Ramipril | 2.500 mg |
| | | HPMC | 0.441 mg |
| | | Pregelatinised starch 1500 | 17.559 mg |
| | | Microcrystalline cellulose 200 | 80.000 mg |
| | | Sodium stearyl fumarate | 0.500 mg |
| | Core total | | 101.000 mg |
| Coating | Opadry AMB yellow 80W32039 | | 4.000 mg |
| Total coated tablet | | | 105.000 mg |

TABLE 28

Coated tablet, 5 mg of ramipril

| | | | |
|---|---|---|---|
| Core | Components | Ramipril | 5.000 mg |
| | | HPMC | 0.882 mg |
| | | Pregelatinised starch 1500 | 19.618 mg |
| | | Microcrystalline cellulose 200 | 75.000 mg |
| | | Sodium stearyl fumarate | 0.500 mg |
| | Core total | | 101.000 mg |
| Coating | Opadry AMB yellow 80W32656 | | 4.000 mg |
| Total coated tablet | | | 105.000 mg |

TABLE 29

Coated tablet, 10 mg of ramipril

| | | | |
|---|---|---|---|
| Core | Components | Ramipril | 10.000 mg |
| | | HPMC | 1.764 mg |
| | | Pregelatinised starch 1500 | 18.736 mg |
| | | Microcrystalline cellulose 200 | 70.000 mg |
| | | Sodium stearyl fumarate | 0.500 mg |
| | Core total | | 101.000 mg |
| Coating | Opadry AMB yellow 80W32880 | | 4.000 mg |
| Total coated tablet | | | 105.000 mg |

The invention claimed is:

1. A capsule which comprises:
   (i) a) w coated tablet(s) comprising 40.5 mg of acetylsalicylic acid and x coated tablet(s) comprising 81 mg of acetylsalicylic acid, wherein w is an integer chosen from 0 and 1, and x is an integer chosen from 0, 1 and 2, such that the total amount of acetylsalicylic acid is from 40.5 to 162 mg and w+x is 1 or 2; or
   b) y coated tablet(s) comprising 50 mg of acetylsalicylic acid and z coated tablet(s) comprising 100 mg of acetylsalicylic acid, wherein y is an integer chosen from 0 and 1, and z is an integer chosen from 0, 1 and 2, such that the total amount of acetylsalicylic acid is from 50 to 200 mg and y+z is 1 or 2;
   (ii) a) s coated tablet(s) comprising 20 mg of simvastatin and t coated tablet(s) comprising 40 mg of simvastatin, wherein s is an integer chosen from 0, 1 and 2, and t is an integer chosen from 0, 1 and 2, such that the total amount of simvastatin is from 20 to 80 mg and s+t is 1 or 2; or
   b) u coated tablet(s) comprising 20 mg of pravastatin or a pharmaceutically acceptable salt thereof and v coated tablet(s) comprising 40 mg of pravastatin or a pharmaceutically acceptable salt thereof, wherein u is an integer chosen from 0, 1 and 2, and v is an integer chosen from 0, 1 and 2, such that the total amount of pravastatin or a pharmaceutically acceptable salt thereof is from 20 to 80 mg and u+v is 1 or 2; and
   (iii) a) p coated tablet(s) comprising 5 mg of lisinopril or a hydrated form, q coated tablet(s) comprising 10 mg of lisinopril or a hydrated form and r coated tablet(s) comprising 20 mg of lisinopril or a hydrated form, wherein p is an integer chosen from 0 and 1, q is an integer chosen from 0 and 1, and r is an integer chosen from 0, 1 and 2, such that the total amount of lisinopril or hydrated form is from 5 to 40 mg and p+q+r is 1, 2 or 3; or
   b) k coated tablet(s) comprising 2.5 mg of ramipril, m coated tablet(s) comprising 5 mg of ramipril and n coated tablet(s) comprising 10 mg of ramipril, wherein k is an integer chosen from 0 and 1, m is an integer chosen from 0 and 1, and n is an integer chosen from 0, 1 and 2, such that the total amount of ramipril is from 2.5 to 20 mg and k+m+n is 1, 2 or 3; or
   c) h coated tablet(s) comprising 2 mg of perindopril or a pharmaceutically acceptable salt thereof, i coated tablet(s) comprising 4 mg of perindopril or a pharmaceutically acceptable salt thereof, and j coated tablet(s) comprising 8 mg of perindopril or a pharmaceutically acceptable salt thereof, wherein h is an integer chosen from 0 and 1, i is an integer chosen from 0 and 1, and j is an integer chosen from 0, 1 and 2, such that the total amount of perindopril or a pharmaceutically acceptable salt thereof is 2 to 16 mg and h+i+j is 1, 2 or 3;

wherein:
the acetylsalicylic acid tablets are coated with a partially hydrolysed polyvinyl alcohol comprising film;
the simvastatin tablets are coated with a hydroxypropylmethyl cellulose comprising film;
the pravastatin or pharmaceutically acceptable salt tablets are coated with a hydroxypropylmethyl cellulose comprising film;
the lisinopril or hydrated form tablets are coated with a partially hydrolysed polyvinyl alcohol comprising film;
the ramipril tablets are coated with a partially hydrolysed polyvinyl alcohol comprising film; and
the perindopril or pharmaceutically acceptable salt tablets are coated with a partially hydrolysed polyvinyl alcohol comprising film, and wherein the presence of the partially hydrolysed polyvinyl alcohol coating film reduces degradation of acetylsalicylic acid to salicylic acid due to moisture and reduces the chemical degradation of ramipril, lisinopril, or perindopril caused by degradation of the acetylsalicylic acid.

2. The capsule according to claim 1, which comprises:
   (i) a) one coated tablet comprising 81 mg of acetylsalicylic acid; or
   b) one coated tablet comprising 100 mg of acetylsalicylic acid;
   (ii) a) two coated tablets each comprising 20 mg of simvastatin; or
   b) two coated tablets each comprising 20 mg of pravastatin sodium salt; and
   (iii) a) one coated tablet comprising 5, 10 or 20 mg of lisinopril dihydrate; or
   b) one coated tablet comprising 2.5, 5 or 10 mg of ramipril; or
   c) one coated tablet comprising 2, 4 or 8 mg of perindopril erbumine salt.

3. The capsule according to claim 2, comprises a combination chosen from:
   (1) one coated tablet comprising 81 mg acetylsalicylic acid, two coated tablets each comprising 20 mg simvastatin and one coated tablet comprising 5 mg lisinopril dihydrate;
   (2) one coated tablet comprising 81 mg acetylsalicylic acid, two coated tablets each comprising 20 mg simvastatin and one coated tablet comprising 10 mg lisinopril dihydrate;
   (3) one coated tablet comprising 81 mg acetylsalicylic acid, two coated tablets each comprising 20 mg simvastatin and one coated tablet comprising 20 mg lisinopril dihydrate;
   (4) one coated tablet comprising 81 mg acetylsalicylic acid, two coated tablets each comprising 20 mg simvastatin and one coated tablet comprising 2.5 mg ramipril;

(5) one coated tablet comprising 81 mg acetylsalicylic acid, two coated tablets each comprising 20 mg simvastatin and one coated tablet comprising 5 mg ramipril;
(6) one coated tablet comprising 81 mg acetylsalicylic acid, two coated tablets each comprising 20 mg simvastatin and one coated tablet comprising 10 mg ramipril;
(7) one coated tablet comprising 81 mg acetylsalicylic acid, two coated tablets each comprising 20 mg simvastatin and one coated tablet comprising 2 mg perindopril erbumine;
(8) one coated tablet comprising 81 mg acetylsalicylic acid, two coated tablets each comprising 20 mg simvastatin and one coated tablet comprising 4 mg perindopril erbumine;
(9) one coated tablet comprising 81 mg acetylsalicylic acid, two coated tablets each comprising 20 mg simvastatin and one coated tablet comprising 8 mg perindopril erbumine;
(10) one coated tablet comprising 81 mg acetylsalicylic acid, two coated tablets each comprising 20 mg pravastatin sodium salt and one coated tablet comprising 5 mg lisinopril dihydrate;
(11) one coated tablet comprising 81 mg acetylsalicylic acid, two coated tablets each comprising 20 mg pravastatin sodium salt and one coated tablet comprising 10 mg lisinopril dihydrate;
(12) one coated tablet comprising 81 mg acetylsalicylic acid, two coated tablets each comprising 20 mg pravastatin sodium salt and one coated tablet comprising 20 mg lisinopril dihydrate;
(13) one coated tablet comprising 81 mg acetylsalicylic acid, two coated tablets each comprising 20 mg pravastatin sodium salt and one coated tablet comprising 2.5 mg ramipril;
(14) one coated tablet comprising 81 mg acetylsalicylic acid, two coated tablets each comprising 20 mg pravastatin sodium salt and one coated tablet comprising 5 mg ramipril;
(15) one coated tablet comprising 81 mg acetylsalicylic acid, two coated tablets each comprising 20 mg pravastatin sodium salt and one coated tablet comprising 10 mg ramipril;
(16) one coated tablet comprising 81 mg acetylsalicylic acid, two coated tablets each comprising 20 mg pravastatin sodium salt and one coated tablet comprising 2 mg perindopril erbumine;
(17) one coated tablet comprising 81 mg acetylsalicylic acid, two coated tablets each comprising 20 mg pravastatin sodium salt and one coated tablet comprising 4 mg perindopril erbumine;
(18) one coated tablet comprising 81 mg acetylsalicylic acid, two coated tablets each comprising 20 mg pravastatin sodium salt and one coated tablet comprising 8 mg perindopril erbumine;
(19) one coated tablet comprising 100 mg acetylsalicylic acid, two coated tablets each comprising 20 mg simvastatin and one coated tablet comprising 5 mg lisinopril dihydrate;
(20) one coated tablet comprising 100 mg acetylsalicylic acid, two coated tablets each comprising 20 mg simvastatin and one coated tablet comprising 10 mg lisinopril dihydrate;
(21) one coated tablet comprising 100 mg acetylsalicylic acid, two coated tablets each comprising 20 mg simvastatin and one coated tablet comprising 20 mg lisinopril dihydrate;
(22) one coated tablet comprising 100 mg acetylsalicylic acid, two coated tablets each comprising 20 mg simvastatin and one coated tablet comprising 2.5 mg ramipril;
(23) one coated tablet comprising 100 mg acetylsalicylic acid, two coated tablets each comprising 20 mg simvastatin and one coated tablet comprising 5 mg ramipril;
(24) one coated tablet comprising 100 mg acetylsalicylic acid, two coated tablets each comprising 20 mg simvastatin and one coated tablet comprising 10 mg ramipril;
(25) one coated tablet comprising 100 mg acetylsalicylic acid, two coated tablets each comprising 20 mg simvastatin and one coated tablet comprising 2 mg perindopril erbumine;
(26) one coated tablet comprising 100 mg acetylsalicylic acid, two coated tablets each comprising 20 mg simvastatin and one coated tablet comprising 4 mg perindopril erbumine;
(27) one coated tablet comprising 100 mg acetylsalicylic acid, two coated tablets each comprising 20 mg simvastatin and one coated tablet comprising 8 mg perindopril erbumine;
(28) one coated tablet comprising 100 mg acetylsalicylic acid, two coated tablets each comprising 20 mg pravastatin sodium salt and one coated tablet comprising 5 mg lisinopril dihydrate;
(29) one coated tablet comprising 100 mg acetylsalicylic acid, two coated tablets each comprising 20 mg pravastatin sodium salt and one coated tablet comprising 10 mg lisinopril dihydrate;
(30) one coated tablet comprising 100 mg acetylsalicylic acid, two coated tablets each comprising 20 mg pravastatin sodium salt and one coated tablet comprising 20 mg lisinopril dihydrate;
(31) one coated tablet comprising 100 mg acetylsalicylic acid, two coated tablets each comprising 20 mg pravastatin sodium salt and one coated tablet comprising 2.5 mg ramipril;
(32) one coated tablet comprising 100 mg acetylsalicylic acid, two coated tablets each comprising 20 mg pravastatin sodium salt and one coated tablet comprising 5 mg ramipril;
(33) one coated tablet comprising 100 mg acetylsalicylic acid, two coated tablets each comprising 20 mg pravastatin sodium salt and one coated tablet comprising 10 mg ramipril;
(34) one coated tablet comprising 100 mg acetylsalicylic acid, two coated tablets each comprising 20 mg pravastatin sodium salt and one coated tablet comprising 2 mg perindopril erbumine;
(35) one coated tablet comprising, 100 mg acetylsalicylic acid two coated tablets each comprising 20 mg pravastatin sodium salt and one coated tablet comprising 4 mg perindopril erbumine; and
(36) one coated tablet comprising 100 mg acetylsalicylic acid, two coated tablets each comprising 20 mg pravastatin sodium salt and one coated tablet comprising 8 mg perindopril erbumine.

4. The capsule according to claim 1, 2 or 3, wherein said capsule is made of hard gelatine.

5. The capsule according to claim 1, 2 or 3, wherein said capsule is made of cellulose.

6. The capsule according to claim 1, wherein all tablets have an unmodified release profile.

7. The capsule according to claim 1, wherein the coatings of each of (i), (ii), or (iii) is a different color.

8. The capsule according to claim 1, wherein the tablets of (ii) are located between the tablets of (i) and (iii) within the capsule.

9. A capsule which comprises:
- (i) a) w coated tablet(s) comprising 40.5 mg of acetylsalicylic acid and x coated tablet(s) comprising 81 mg of acetylsalicylic acid, wherein w is an integer chosen from 0 and 1, and x is an integer chosen from 0, 1 and 2, such that the total amount of acetylsalicylic acid is from 40.5 to 162 mg and w+x is 1 or 2; or
  - b) y coated tablet(s) comprising 50 mg of acetylsalicylic acid and z coated tablet(s) comprising 100 mg of acetylsalicylic acid, wherein y is an integer chosen from 0 and 1, and z is an integer chosen from 0, 1 and 2, such that the total amount of acetylsalicylic acid is from 50 to 200 mg and y+z is 1 or 2;
- (ii) a) s coated tablet(s) comprising 20 mg of simvastatin and t coated tablet(s) comprising 40 mg of simvastatin, wherein s is an integer chosen from 0, 1 and 2, and t is an integer chosen from 0, 1 and 2, such that the total amount of simvastatin is from 20 to 80 mg and s+t is 1 or 2; or
  - b) u coated tablet(s) comprising 20 mg of pravastatin or a pharmaceutically acceptable salt thereof and v coated tablet(s) comprising 40 mg of pravastatin or a pharmaceutically acceptable salt thereof, wherein u is an integer chosen from 0, 1 and 2, and v is an integer chosen from 0, 1 and 2, such that the total amount of pravastatin or a pharmaceutically acceptable salt thereof is from 20 to 80 mg and u+v is 1 or 2; and
- (iii) a) p coated tablet(s) comprising 5 mg of lisinopril or a hydrated form, q coated tablet(s) comprising 10 mg of lisinopril or a hydrated form and r coated tablet(s) comprising 20 mg of lisinopril or a hydrated form, wherein p is an integer chosen from 0 and 1, q is an integer chosen from 0 and 1, and r is an integer chosen from 0, 1 and 2, such that the total amount of lisinopril or hydrated form is from 5 to 40 mg and p+q+r is 1, 2 or 3; or
  - b) k coated tablet(s) comprising 2.5 mg of ramipril, m coated tablet(s) comprising 5 mg of ramipril and n coated tablet(s) comprising 10 mg of ramipril, wherein k is an integer chosen from 0 and 1, m is an integer chosen from 0 and 1, and n is an integer chosen from 0, 1 and 2, such that the total amount of ramipril is from 2.5 to 20 mg and k+m+n is 1, 2 or 3; or
  - c) h coated tablet(s) comprising 2 mg of perindopril or a pharmaceutically acceptable salt thereof, i coated tablet(s) comprising 4 mg of perindopril or a pharmaceutically acceptable salt thereof, and j coated tablet(s) comprising 8 mg of perindopril or a pharmaceutically acceptable salt thereof, wherein h is an integer chosen from 0 and 1, i is an integer chosen from 0 and 1, and j is an integer chosen from 0, 1 and 2, such that the total amount of perindopril or a pharmaceutically acceptable salt thereof is 2 to 16 mg and h+i+j is 1, 2 or 3;

wherein:
the acetylsalicylic acid tablets are coated with a partially hydrolysed polyvinyl alcohol comprising film;
the simvastatin tablets are coated with a hydroxypropylmethyl cellulose comprising film;
the pravastatin or pharmaceutically acceptable salt tablets are coated with a hydroxypropylmethyl cellulose comprising film;
the lisinopril or hydrated form tablets are coated with a partially hydrolysed polyvinyl alcohol comprising film;
the ramipril tablets are coated with a partially hydrolysed polyvinyl alcohol comprising film; and
the perindopril or pharmaceutically acceptable salt tablets are coated with a partially hydrolysed polyvinyl alcohol comprising film,
wherein the tablets described in (i), (ii) or (iii) are immediately released within 60 minutes.

10. A capsule consisting essentially of:
- (i) a) w coated tablet(s) comprising 40.5 mg of acetylsalicylic acid and x coated tablet(s) comprising 81 mg of acetylsalicylic acid, wherein w is an integer chosen from 0 and 1, and x is an integer chosen from 0, 1 and 2, such that the total amount of acetylsalicylic acid is from 40.5 to 162 mg and w+x is 1 or 2; or
  - b) y coated tablet(s) comprising 50 mg of acetylsalicylic acid and z coated tablet(s) comprising 100 mg of acetylsalicylic acid, wherein y is an integer chosen from 0 and 1, and z is an integer chosen from 0, 1 and 2, such that the total amount of acetylsalicylic acid is from 50 to 200 mg and y+z is 1 or 2;
- (ii) a) s coated tablet(s) comprising 20 mg of simvastatin and t coated tablet(s) comprising 40 mg of simvastatin, wherein s is an integer chosen from 0, 1 and 2, and t is an integer chosen from 0, 1 and 2, such that the total amount of simvastatin is from 20 to 80 mg and s+t is 1 or 2; or
  - b) u coated tablet(s) comprising 20 mg of pravastatin or a pharmaceutically acceptable salt thereof and v coated tablet(s) comprising 40 mg of pravastatin or a pharmaceutically acceptable salt thereof, wherein u is an integer chosen from 0, 1 and 2, and v is an integer chosen from 0, 1 and 2, such that the total amount of pravastatin or a pharmaceutically acceptable salt thereof is from 20 to 80 mg and u+v is 1 or 2; and
- (iii) a) p coated tablet(s) comprising 5 mg of lisinopril or a hydrated form, q coated tablet(s) comprising 10 mg of lisinopril or a hydrated form and r coated tablet(s) comprising 20 mg of lisinopril or a hydrated form, wherein p is an integer chosen from 0 and 1, q is an integer chosen from 0 and 1, and r is an integer chosen from 0, 1 and 2, such that the total amount of lisinopril or hydrated form is from 5 to 40 mg and p+q+r is 1, 2 or 3; or
  - b) k coated tablet(s) comprising 2.5 mg of ramipril, m coated tablet(s) comprising 5 mg of ramipril and n coated tablet(s) comprising 10 mg of ramipril, wherein k is an integer chosen from 0 and 1, m is an integer chosen from 0 and 1, and n is an integer chosen from 0, 1 and 2, such that the total amount of ramipril is from 2.5 to 20 mg and k+m+n is 1, 2 or 3; or
  - c) h coated tablet(s) comprising 2 mg of perindopril or a pharmaceutically acceptable salt thereof, i coated tablet(s) comprising 4 mg of perindopril or a pharmaceutically acceptable salt thereof, and j coated tablet(s) comprising 8 mg of perindopril or a pharmaceutically acceptable salt thereof, wherein h is an integer chosen from 0 and 1, i is an integer chosen from 0 and 1, and j is an integer chosen from 0, 1 and 2, such that the total amount of perindopril or a pharmaceutically acceptable salt thereof is 2 to 16 mg and h+i+j is 1, 2 or 3;

wherein:
the acetylsalicylic acid tablets are coated with a partially hydrolysed polyvinyl alcohol comprising film;
the simvastatin tablets are coated with a hydroxypropylmethyl cellulose comprising film;
the pravastatin or pharmaceutically acceptable salt tablets are coated with a hydroxypropylmethyl cellulose comprising film;
the lisinopril or hydrated form tablets are coated with a partially hydrolysed polyvinyl alcohol comprising film;

the ramipril tablets are coated with a partially hydrolysed polyvinyl alcohol comprising film; and the perindopril or pharmaceutically acceptable salt tablets are coated with a partially hydrolysed polyvinyl alcohol comprising film.

11. A method for the prevention of cardiovascular diseases in high-risk populations, which comprises administering the capsule according to claim 1 to a person or patient from said high-risk populations in need thereof.

12. The method according to claim 11 wherein high-risk populations are people of more than 55 years of age, patients with a background of angor pectoris, ictus, arteriosclerosis, intermittent claudication, diabetes, coronary disease, peripheral vascular disease, altered platelet function, haemodialysis, hypercholesterolaemia, hypertension, myocardial infarction, congestive heart failure, ischaemia, nephropathy, cardiac arrest or restenosis, smokers, obese people and sedentary people.

* * * * *